(12) United States Patent
Veenstra et al.

(10) Patent No.: US 11,957,473 B2
(45) Date of Patent: Apr. 16, 2024

(54) ECG ELECTRODE CONNECTOR AND ECG CABLE

(71) Applicant: KONINKLIJKE PHILIPS N.V., Eindhoven (NL)

(72) Inventors: Hugo Veenstra, Kleine Brogel (BE); Frank Verbakel, Helmond (NL)

(73) Assignee: Koninklijke Philips N.V., Eindhoven (NL)

(*) Notice: Subject to any disclaimer, the term of this patent is extended or adjusted under 35 U.S.C. 154(b) by 834 days.

(21) Appl. No.: 16/970,098

(22) PCT Filed: Feb. 6, 2019

(86) PCT No.: PCT/EP2019/052875
§ 371 (c)(1),
(2) Date: Aug. 14, 2020

(87) PCT Pub. No.: WO2019/162089
PCT Pub. Date: Aug. 29, 2019

(65) Prior Publication Data
US 2021/0030293 A1 Feb. 4, 2021

(30) Foreign Application Priority Data
Feb. 20, 2018 (EP) .................................... 18157591

(51) Int. Cl.
*A61B 5/274* (2021.01)
*A61B 5/25* (2021.01)
(52) U.S. Cl.
CPC ........ *A61B 5/274* (2021.01); *A61B 2562/182* (2013.01); *A61B 2562/222* (2013.01); *A61B 2562/227* (2013.01)
(58) Field of Classification Search
CPC .............. A61B 5/274; A61B 2562/182; A61B 2562/222; A61B 2562/227; A61B 5/25;
(Continued)

(56) References Cited

U.S. PATENT DOCUMENTS 3,620,208 A 11/1971 Ravin
3,620,209 A 11/1971 Higley
(Continued)

FOREIGN PATENT DOCUMENTS

KR 1020160037662 A 4/2016
WO 200065994 A1 11/2000
(Continued)

OTHER PUBLICATIONS

International Search Report and Written Opinion of PCT/PCT/EP20019/052875, dated Apr. 20, 2019.
2016id01707.

*Primary Examiner* — Adam Z Minchella (57) ABSTRACT

The present invention relates to an ECG electrode connector (1) and an ECG cable. To eliminate a trunk cable of a conventional ECG cable arrangement, the ECG electrode connector (1) is configured for mechanically and electrically connecting an ECG electrode with a lead wire. It comprises a connection arrangement (10) for mechanically connecting the ECG electrode connector (1) with an ECG electrode (100), a lead wire terminal (14) for connection with a signal line (301) of a lead wire (300), a shield terminal (15) for connection with a shield (302) of the lead wire (300), an electrode contact (17) for contacting an electrical contact (101) of the ECG electrode (100), a voltage clamping element (13) coupled between the lead wire terminal (14) and the shield terminal (15), and a resistor (16) coupled between the lead wire terminal (14) and the electrode contact (17).

9 Claims, 8 Drawing Sheets (58) Field of Classification Search
CPC ..... A61B 5/308; A61B 5/318; A61B 2562/22; A61B 2562/225
See application file for complete search history.

(56) References Cited

U.S. PATENT DOCUMENTS

| | | | |
|---|---|---|---|
| 5,336,253 A | 8/1994 | Gordon | |
| 6,246,902 B1* | 6/2001 | Naylor | A61B 5/30 600/509 |
| 6,895,555 B1 | 5/2005 | Ando | |
| 8,427,181 B2 | 4/2013 | Chetelat | |
| 10,304,561 B2 | 5/2019 | Shin | |
| 2009/0093687 A1* | 4/2009 | Telfort | A61B 5/0215 600/300 |
| 2011/0092833 A1* | 4/2011 | Farrior | A61B 5/318 600/508 |
| 2011/0313305 A1 | 12/2011 | Rantala | |
| 2012/0143034 A1* | 6/2012 | Gaw | A61B 5/274 600/393 |
| 2013/0085402 A1* | 4/2013 | Callahan | A61B 5/7217 600/509 |
| 2014/0088394 A1 | 3/2014 | Sunderland | |
| 2016/0206224 A1 | 7/2016 | Marek | |

FOREIGN PATENT DOCUMENTS

| | | | | |
|---|---|---|---|---|
| WO | WO-0065994 A1 * | 11/2000 | | A61B 5/0428 |
| WO | 2017220328 A1 | 12/2017 | | |

* cited by examiner

ECG ELECTRODE CONNECTOR AND ECG CABLE

FIELD OF THE INVENTION

The present invention relates to an ECG (electrocardiography) electrode connector and an ECG cable.

This application is the U.S. National Phase application under 35 U.S.C. § 371 of International Application No. PCT/EP2019/052875, filed on Feb. 6, 2019, which claims the benefit of European Application Serial No. 18157591.1, filed Feb. 20, 2018. These applications are hereby incorporated by reference herein.

BACKGROUND OF THE INVENTION

A typical configuration for a medical-grade ECG measurement system makes use of a measurement unit (e.g. a mobile unit or an ECG monitor), a trunk cable, a trunk unit, a lead set with grabbers or snappers, and ECG electrodes. The electrodes are placed on the body. The lead set connects to the electrodes using snappers or grabbers. Each electrode is connected to the trunk unit via a lead, typically a shielded cable. Inside the grabber or snapper, an inductor is sometimes used to provide enhanced protection and filtering for electrosurgery (ESU) signals. This is important for lead sets used in the operating theatre. Inside the trunk, safety resistors are often placed to protect the measurement unit against high voltages that can occur during defibrillation treatments. Additional safety elements such as sidactors are used inside the measurement unit to limit the maximum voltage on the input of the ECG measurement unit.

Snappers and grabbers are both commonly used as ECG electrode connector. They are electrically equivalent, and the choice between grabber or snapper depends on the preference of the user. Herein, reference is generally made to ECG electrode connector, and all technical details apply to all embodiments, including snappers, grabbers or clamping means, if not specified otherwise.

Conventional ECG electrode connectors have a single electrical connection to the lead wire (also called lead), which connects to the trunk unit. The lead wire is a shielded cable. The shield of this cable ends (unconnected) at the attach point from the cable to the ECG electrode connector. Inside the ECG electrode connector, an inductor can be used for ECG electrode connectors that are part of a so-called orange lead set, intended for use in the operating theatre. This inductor provides additional filtering between electrode and ECG measurement unit when the patient is undergoing electrosurgery treatments.

The conventional hardware between the measurement unit and the ECG electrode is rather bulky and heavy, making it uncomfortable, in particular for mobile applications, e.g. when the patient can freely move outside the bed. Hence, there is a need for reducing the size and weight of this hardware.

WO 2017/220328 A1 discloses a medical coupling unit for electrical signal transmission between the medical coupling unit and a medical sensor coupled to the medical coupling unit. The medical coupling unit comprises a coupling-side connector comprising a plurality of first electrical contacts in or on a first surface and a plurality of second electrical contacts in or on a second surface opposite the first surface, and a connector interface for analyzing electrical signals available at one or more of the plurality of first and second electrical contacts to detect one or more of presence of a medical sensor coupled to the medical coupling unit, the type of medical sensor coupled to the medical coupling unit, and the orientation of a sensor-side connector of a medical sensor coupled to the medical coupling unit. Further, a sensor-side connector is disclosed.

SUMMARY OF THE INVENTION

It is an object of the present invention to provide an ECG electrode connector and an ECG cable, by which the size and weight of the hardware between the measurement unit and the ECG electrode are reduced.

In a first aspect of the present invention an ECG electrode connector for mechanically and electrically connecting an ECG electrode with a lead wire is presented, the ECG electrode connector comprising:
- a connection arrangement for mechanically connecting the ECG electrode connector with an ECG electrode,
- a lead wire terminal for connection with a signal line of a lead wire,
- a shield terminal for connection with a shield of the lead wire,
- an electrode contact for contacting an electrical contact of the ECG electrode,
- a voltage clamping element coupled between the lead wire terminal and the shield terminal, and
- a resistor coupled between the lead wire terminal and the electrode contact.

In a further aspect of the present invention an ECG cable is presented comprising:
- one or more lead wires,
- one or more ECG electrode connectors comprising at least one ECG electrode connector as disclosed herein, wherein one lead wire is provided per ECG electrode and each ECG electrode connector is connected to a respective lead wire to mechanically and electrically connect the lead wire with an ECG electrode.

Preferred embodiments of the invention are defined in the dependent claims. It shall be understood that the claimed ECG cable has similar and/or identical preferred embodiments as the claimed ECG electrode connector, in particular as defined in the dependent claims and as disclosed herein.

The present invention is based on the idea to incorporate the safety network comprising at least one or more resistors and voltage clamping elements (preferably sidactors; alternatively neons or trigards), and optionally one or more inductors, into the ECG electrode connector. The trunk unit can thus be eliminated completely, leading to a substantial reduction in size and weight of the complete hardware required between measurement unit and ECG electrode. The ECG electrode connector is connected to the measurement unit via a lead wire. From an electrical perspective, the measurement system using conventional ECG electrode connectors and a trunk unit on the one hand and a measurement system using ECG electrode connectors as disclosed herein on the other hand are substantially equal and their performance is substantially identical.

In an embodiment the ECG electrode connector further comprises an inductor coupled between the lead wire terminal and the electrode contact, in particular between the resistor and the electrode contact. This inductor provides enhanced protection and filtering for ESU signals.

In another embodiment the resistor comprises two or more resistor elements coupled in series. For instance, multiple lower-value resistor elements can be used in series to allow for an attractive low-cost connector design. The resistor elements can then also be reduced in size compared to a single resistor.

The ECG electrode connector may further comprise a ground plane coupled to the shield terminal and arranged between the resistor and the voltage clamping element on the one side and the ECG electrode on the other side, when the connector and the ECG electrode are connected. This ground plane then acts as a ground shield, which reduces overall sensitivity to interference.

The connection arrangement of the ECG electrode connector may comprise a clamping arrangement or a snapping arrangement or a grabbing arrangement. A conventional mechanical design may thus be used. Other designs are possible.

In one embodiment the ECG electrode connector comprises a single lead wire terminal, a single shield terminal, a single voltage clamping element and a single resistor. This embodiment is particularly used for ECG electrodes which shall not be used for respiration measurement.

A medical-grade ECG measurement system shall generally provide the capability to measure respiration, i.e. at least some ECG electrodes (usually RA, LA and LL) shall be used for respiration measurement. The bio-impedance from the human body seen between electrodes is modulated by respiration. Thus, respiration can be measured via an impedance measurement system in the ECG measurement unit.

In an ECG measurement system using a classical trunk cable and lead set there exist different types of lead set that are intended for various use cases. In particular, an orange lead set exists that is intended for use in the operating theatre. In the orange lead set, extra protection and filtering by means of a series inductor in each lead is used in the lead set. When the orange lead set is used, the respiration measurement function of the ECG measurement unit is not reliable and must not be used. This is because of the presence of inductors in series with the electrodes, which attenuate the modulation and demodulation signals used in the respiration detection system.

Hence, in an embodiment the ECG electrode connector further comprises a second lead wire terminal for connection with a second signal line of the lead wire, a second voltage clamping element coupled between the second lead wire terminal and the shield terminal, and a second resistor coupled between the second lead wire terminal and the electrode contact. Thus, a duplicate safety network is provided to support improved respiration detection accuracy.

In this embodiment it may be preferred that one end of the inductor is coupled to the electrode contact and the other end of the inductor is coupled to the resistor and the second resistor, i.e. both resistors connect at one end to the same inductor.

In another embodiment a second inductor is provided that is coupled between the second lead wire terminal and the electrode contact, in particular between the second resistor and the electrode contact. In this way the connection point where the two paths merge is moved closer to the ECG electrode which further improves the accuracy of the respiration measurement system.

In the latter embodiment a second electrode contact may be provided for contacting a second electrical contact of the ECG electrode, wherein the inductor is coupled to the electrode contact and the second inductor is coupled to the second electrode contact. By means of these separated contacts to the ECG electrode, a simple detection method is supported to detect if the ECG electrode connector is connected to an ECG electrode.

The ECG electrode connector may further comprise a second shield terminal for connection with the shield of the lead wire, wherein the second voltage clamping element is coupled between the second lead wire terminal and the second shield terminal. This further improves the safety.

In a practical implementation the resistor may have a resistance of at least 2 kΩ, in particular in the range of 2 kΩ to 50 kΩ or in the range of 5 kΩ to 20 kΩ, e.g. 10 kΩ.

The proposed ECG cable comprises one or more lead wires and one or more of the proposed ECG electrode connectors. It may further comprise at least two respiration type lead wires, each having two signal lines, and at least two ECG electrode connectors including a duplicate safety network as described above, each of said at least two ECG electrode connectors being connected to a respective respiration type lead wire.

The ECG cable may further comprise at least one non-respiration type lead wire, each having a single signal lines and at least one ECG electrode connector having a single safety network as described above, said at least one ECG electrode connector being connected to a respective non-respiration type lead wire.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE EMBODIMENTS

Figure 1:
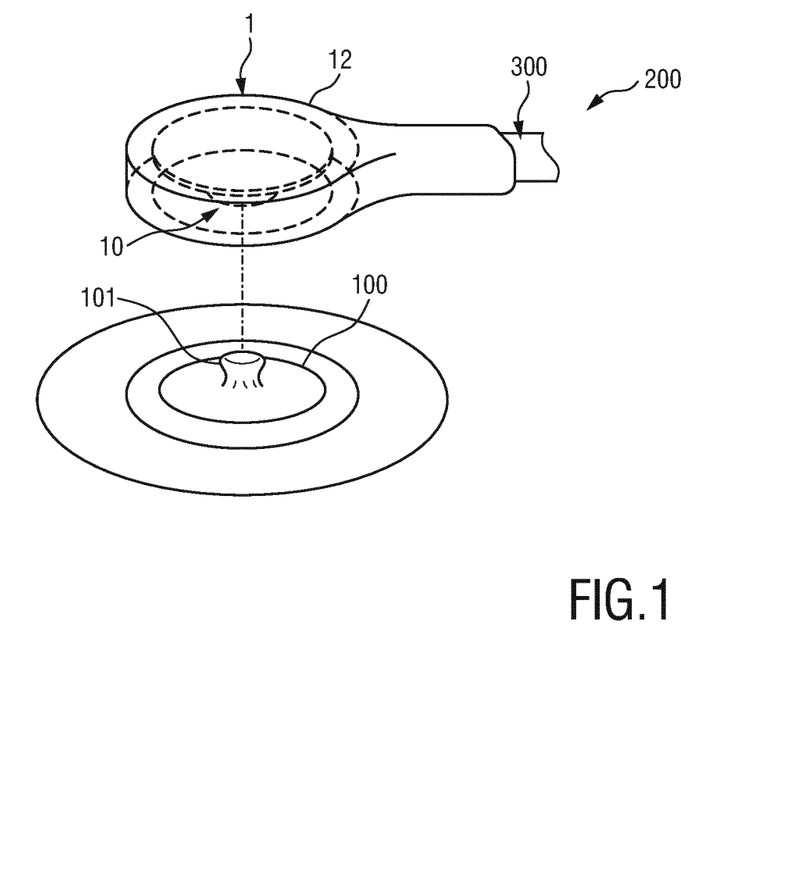
FIG. 1 shows a perspective view of an embodiment of an ECG electrode and an ECG cable comprising an ECG electrode connector according to the present invention.
Figure 2:
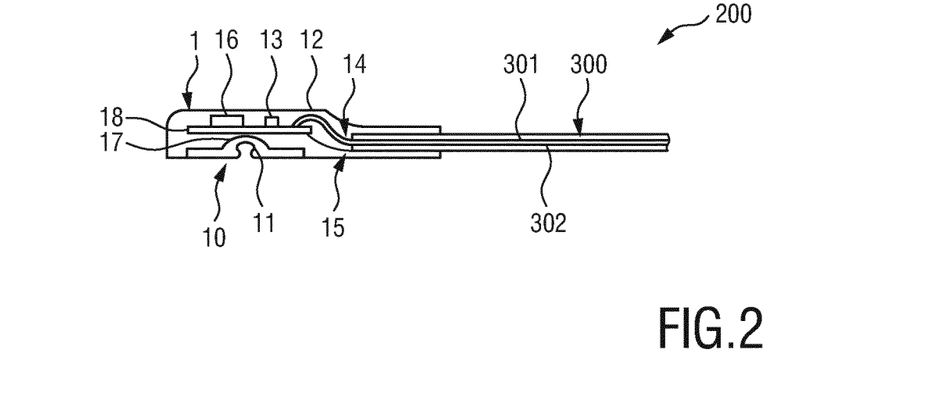
FIG. 2 shows a cross-sectional view of an ECG cable according to the present invention.

FIG. 1 shows a perspective view of an embodiment of an ECG electrode 100 and an ECG cable 200 comprising an ECG electrode connector 1 and FIG. 2 shows a cross-sectional view of the ECG cable 200 according to the present invention. The ECG cable 200 comprises one (or more) lead wire(s) 300 and one (or more) ECG electrode connector(s) 1. Generally, one lead wire 300 is provided per ECG electrode 100 and each ECG connector 1 is connected to a respective lead wire 300. The one (or more) lead wire(s) may be combined into a common cable connecting the one (or more) ECG electrode(s) with an ECG measurement unit (not shown), e.g. a mobile unit or an ECG monitor. A lead wire 300 generally comprises a signal line 301 carrying the measured signal and a shield 302 for shielding the signal line 301 from disturbing radiation.

The ECG electrode connector 1 comprises a connection arrangement 10 for mechanically connecting the ECG electrode connector 1 with the ECG electrode 100. The connection arrangement 10 may generally comprise any kind of connection means that allow a fixed mechanical connection of the ECG electrode connector 1 to the ECG electrode 100 during use. For instance, it may comprises a clamping arrangement or a snapping arrangement or a grabbing arrangement. In the embodiment shown in FIGS. 1 and 2 the connection arrangement 10 of the ECG electrode connector 1 comprises a female connection portion 11 that engages with a corresponding male portion 101 the ECG electrode 100, said male portion representing an electrical contact of the ECG electrode. For instance, the housing 12 of the ECG electrode connector 1 may be designed accordingly.

The ECG electrode connector 1 further comprises safety elements (also called protection elements), in particular a voltage clamping element 13 (in this embodiment a sidactor) that is coupled between a lead wire terminal 14 and a shield terminal 15 and a resistor 16 that is coupled between the lead wire terminal 14 and an electrode contact 17. The voltage clamping element 13 and the resistor 16 may e.g. be arranged on a PCB 18 that is mounted inside the ECG electrode connector 1 or may be coupled between respective wires (not shown).

Generally, it may be distinguished between ECG electrodes (and corresponding ECG electrode connectors) that can take part in a 4-wire respiration detection system (usually the ECG electrodes RA, LA and LL) and all other ECG electrodes (and corresponding ECG electrode connectors) that need not to take part in a 4-wire respiration detection system (usually the ECG electrodes RL and V1-V6). The ECG electrodes (and corresponding ECG electrode connectors) that are not used to measure respiration do not require dual protection circuitry.

Figure 3:
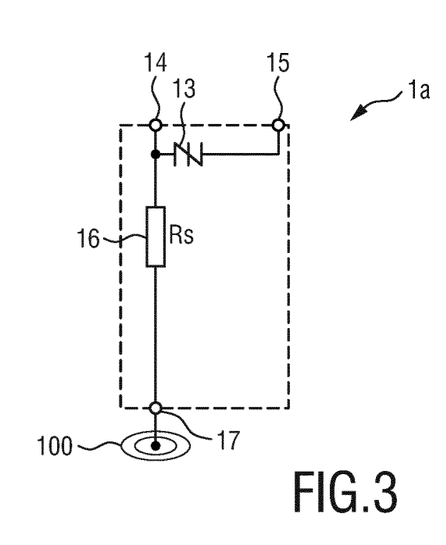
FIG. 3 shows a circuit diagram of a first embodiment of an ECG electrode connector according to the present invention.

FIG. 3 shows a circuit diagram of a first embodiment of an ECG electrode connector 1a according to the present invention that may not be used for respiration measurement. The ECG electrode connector 1a comprises, besides the electrode contact 17, a single lead wire terminal 14, a single shield terminal 15, a single voltage clamping element 13 and a single resistor 16 (Rs). The voltage clamping element 13 is coupled between the lead wire terminal 14 and the shield terminal 15. The resistor 16 is coupled between the lead wire terminal 14 and the electrode contact 17.

Figure 4:
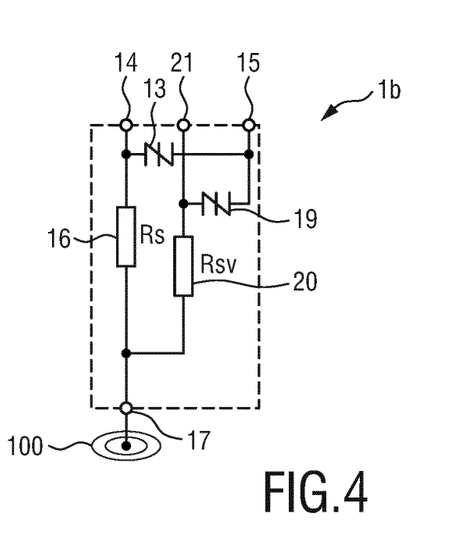
FIG. 4 shows a circuit diagram of a second embodiment of an ECG electrode connector according to the present invention.

FIG. 4 shows a circuit diagram of a second embodiment of an ECG electrode connector 1b according to the present invention that may be used for respiration measurement in a 4-wire respiration detection system (using two ECG electrodes, each connected to e.g. one such ECG electrode connector 1b). In addition to the elements of the first embodiment of an ECG electrode connector 1a shown in FIG. 3, the ECG electrode connector 1b further comprises a second voltage clamping element 19, a second resistor 20 (Rsv) and a second lead wire terminal 21 for connection with a second signal line (not shown) of the lead wire 300. The second voltage clamping element 19 is coupled between the second lead wire terminal 21 and the shield terminal 15. The second resistor 20 is coupled between the second lead wire terminal 21 and the electrode contact 17.

Figure 5:
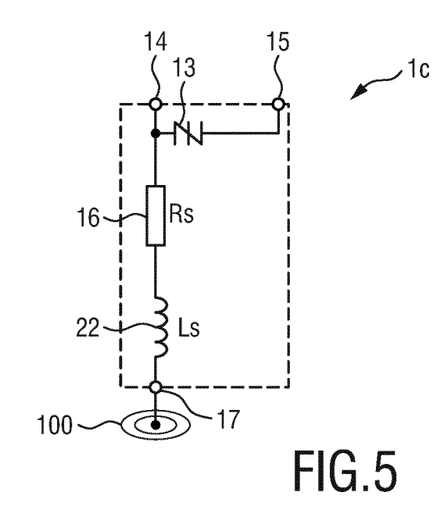
FIG. 5 shows a circuit diagram of a third embodiment of an ECG electrode connector according to the present invention.

FIG. 5 shows a circuit diagram of a third embodiment of an ECG electrode connector 1c according to the present invention that may not be used for respiration measurement. In addition to the elements of the first embodiment of the ECG electrode connector 1a shown in FIG. 3, the ECG electrode connector 1c further comprises an inductor 22 (Ls) coupled between the lead wire terminal 14 and the electrode contact 17, in particular between the resistor 16 and the electrode contact 17. The inductor provides enhanced protection and filtering between the ECG electrode and the ECG measurement unit when the patient is undergoing electrosurgery (ESU) treatments, which is particularly important for lead sets used in the operating theatre.

Figure 6:
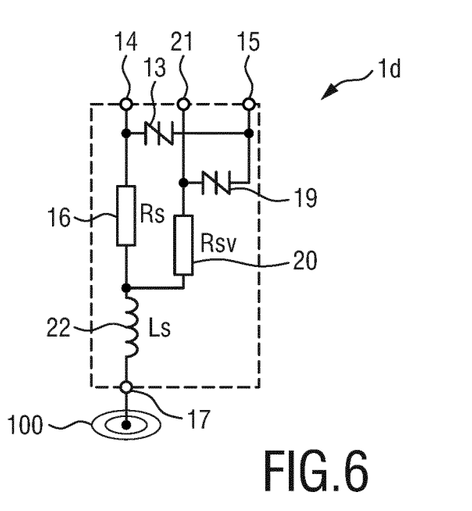
FIG. 6 shows a circuit diagram of a fourth embodiment of an ECG electrode connector according to the present invention.

FIG. 6 shows a circuit diagram of a fourth embodiment of an ECG electrode connector 1d according to the present invention that may be used for respiration measurement (using two ECG electrodes, each connected to e.g. one such ECG electrode connector 1d). In addition to the elements of the second embodiment of the ECG electrode connector 1b shown in FIG. 4, the ECG electrode connector 1d further comprises an inductor 22 (Ls) coupled between the second lead wire terminal 21 and the electrode contact 17, in particular between the second resistor 20 and the electrode contact 17. One end of the inductor 22 is coupled to the electrode contact 17 and the other end of the inductor 22 is coupled to the resistor 16 and the second resistor 20.

Figure 7:
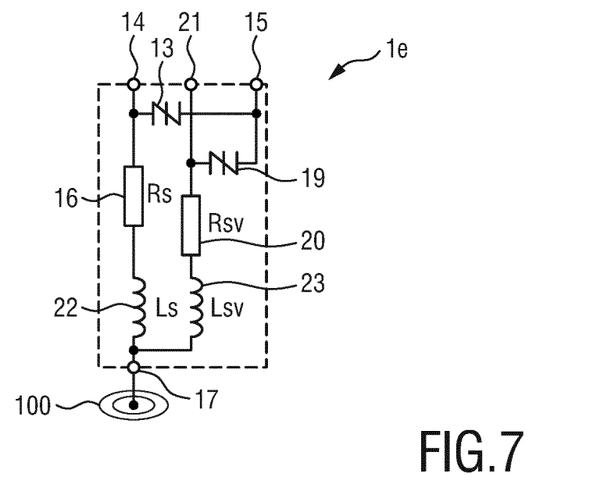
FIG. 7 shows a circuit diagram of a fifth embodiment of an ECG electrode connector according to the present invention.

The accuracy of the respiration impedance measurement can be further improved by duplicating the inductor inside the ECG electrode connector. FIG. 7 shows a circuit diagram of a fifth embodiment of an ECG electrode connector 1e according to the present invention making use of this option. In addition to the fourth embodiment of the ECG electrode connector 1d shown in FIG. 6, the ECG electrode connector 1e further comprises a second inductor 23 (Lsv) coupled between the second lead wire terminal 21 and the electrode contact 17, in particular between the second resistor 20 and the electrode contact 17. The measured impedance for the ECG electrode connector 1e equals Rbody (resistance of the body)+2 Z_electrode (impedance of the ECG electrode), which is an improvement over the ECG electrode connector with a single inductor, e.g. the ECG electrode connector 1d shown in FIG. 5, since the impedance of the inductor Ls plays no role in the measured impedance.

Figure 8:
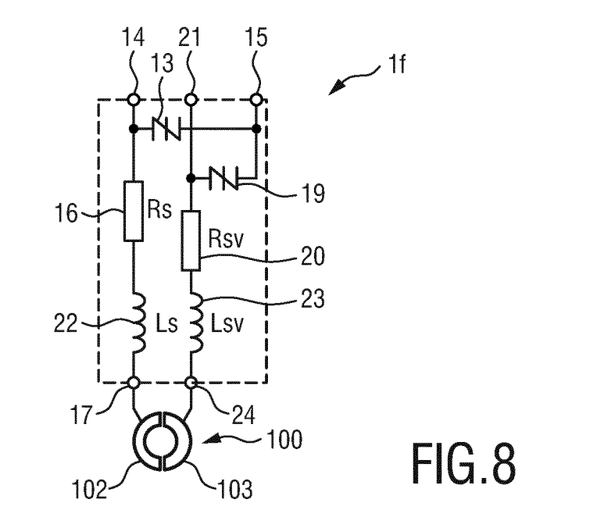
FIG. 8 shows a circuit diagram of a sixth embodiment of an ECG electrode connector according to the present invention.

FIG. 8 shows a circuit diagram of a sixth embodiment of an ECG electrode connector 1f according to the present invention. In addition to the fifth embodiment of the ECG electrode connector 1e shown in FIG. 7, the ECG electrode connector 1f further comprises a second electrode contact 24. In this embodiment the electrical contact of the ECG electrode may be split into two electrical contacts 102, 103, wherein a first electrical contact 102 is connected with the first electrode contact 17 and the second electrical contact 103 is connected with the second electrode contact 24. The two electrical contacts 102, 103 are, however, preferably connected electrically (i.e. short-circuited) within the ECG electrode 100. The dual connection of the ECG electrode connector 1f to the ECG electrode 100 provides the advantage that it enables reliable detection of the ECG electrode connector 1f being connected to the ECG electrode 100 (if the two electrode contacts 17 and 24 being short-circuited) or not (if the two electrode contacts 17 and 24 being open-circuited).

In a 4-wire respiration configuration, as e.g. shown in FIGS. 4, 6, 7 and 8, the safety resistors 16 (Rs) and 20 (Rsv) do not dissipate much energy during defibrillation, e.g. typically <1 J each at Rs=Rsv=10 kΩ for a single defibrillation pulse. Relatively small resistors (in size) are sufficient to dissipate this energy reliably. However, next to the energy rating, the resistors should also be capable of handling the defibrillation voltage of up to 5 kV. This usually requires large resistors (in size). Smaller resistors are possible by using potting techniques. A further alternative is to split the resistors Rs and Rsv into multiple resistors in series as shown in FIG. 9.

Figure 9:
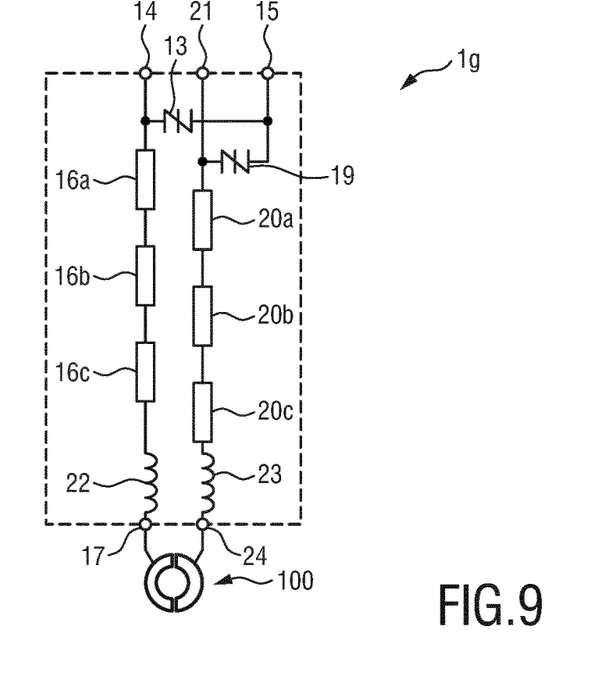
FIG. 9 shows a circuit diagram of a seventh embodiment of an ECG electrode connector according to the present invention.

FIG. 9 shows a circuit diagram of a seventh embodiment of an ECG electrode connector 1g according to the present invention. Different from the sixth embodiment of the ECG electrode connector 1f shown in FIG. 8, in the ECG electrode connector 1g the resistor 16 comprises two or more resistor elements 16a-16c coupled in series and the second resistor 20 comprises two or more resistor elements 20a-20c coupled in series. For instance, in the embodiment shown in FIG. 9 the resistor 16 is split into three resistor elements of equal resistance value and the resistor 20 is split into three resistor elements of equal resistance value. In other embodiment only the resistor 16 or the second resistor 20 comprises two or more resistor elements. In embodiments of the ECG electrode connectors having a single resistor 16 only, the same idea may be used as well, i.e. the resistor 16 may comprise two or more resistor elements 16a-16c as well.

In the embodiment shown in FIG. 9, n resistor elements (n=3 in the exemplary embodiment shown in FIG. 9) are used in series, each of value Rs/n and Rsv/n. The energy dissipation per resistor element and voltage across each resistor element reduces proportionally with n, and therefore each resistor element can be much smaller and cheaper, leading to a more compact and cheaper overall solution for the ECG electrode connector. Moreover, the series connection can be constructed in an arbitrary physical configuration (e.g. straight, circular, etc.) which allows for a more attractive design of the ECG electrode connector.

In further embodiments of the ECG electrode connector, the inductor(s) 22, 23 can be split and implemented from a series network in a similar fashion as the resistors 16, 20 in the embodiment shown in FIG. 9.

Figure 10:
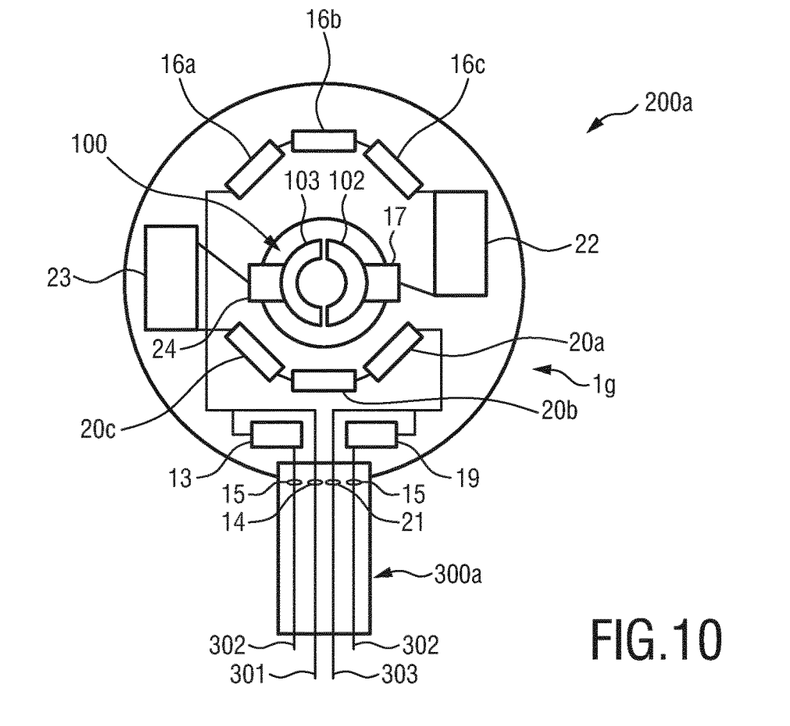
FIG. 10 shows a top view of a practical implementation of an ECG cable including the ECG electrode connector shown in FIG. 9.

A top view of a practical implementation of an ECG cable 200a including the ECG electrode connector 1g shown in FIG. 9 is depicted in FIG. 10. The lead wire 300a comprises a first signal line 301 connected with the first lead wire terminal 14, a second signal line 303 connected with the second lead wire terminal 21 and a shield 302 connected with the shield terminal 15. This ECG cable 200a thus provides 4-wire respiration support by means of duplicate safety networks and two signal connections to a 2-wire shielded lead wire 300a. Split resistors (in this case each resistor being split into three resistor elements) enable resistor elements of small physical size and flexible positioning and layout of the resistor networks. Further, two separate contacts 17, 24 to the ECG electrode 100 support inside the ECG measurement unit simple detection of the ECG electrode 100 being attached or not. Still further, embedded voltage clamping elements 13, 19 limit the highest voltage in the lead wire and thus relax the voltage handling requirement for the lead wire.

Generally, the inductor is only needed if the ECG electrode connector is intended for use in the operating theatre. If usage in the operating theatre is excluded, ECG electrode connector versions without inductor can be envisaged as e.g. shown in FIGS. 11 and 12 in a top view. These designs can be smaller in physical size for increased patient comfort.

Figure 11:
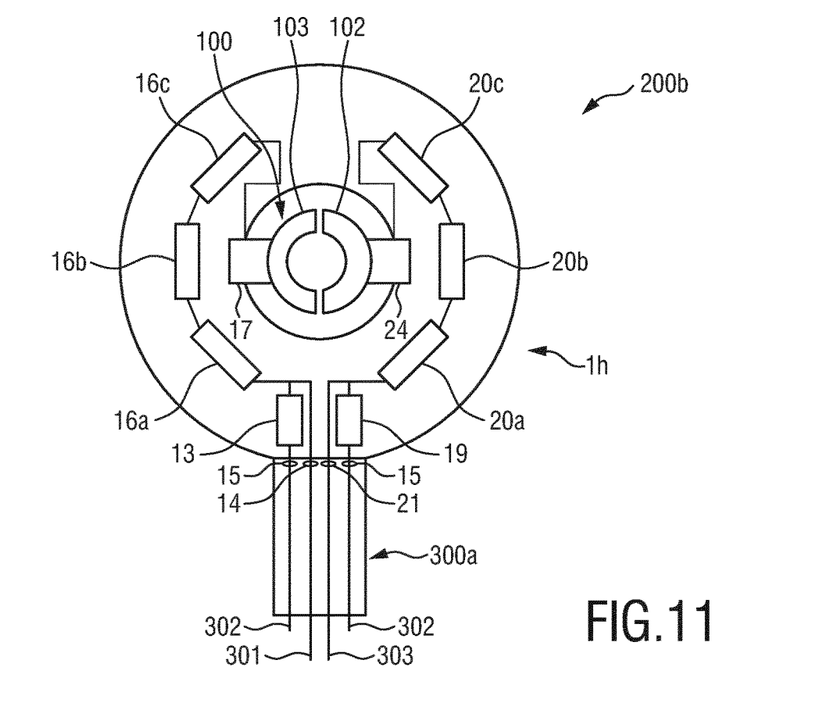
FIG. 11 shows a top view of an ECG cable including an embodiment of an ECG electrode connector for respiration measurement.

FIG. 11 shows a top view of an ECG cable 200b including an embodiment of an ECG electrode connector 1h that supports 4-wire respiration measurement using dual protection networks and is intended for leads that can be used for respiration measurements (e.g. RA, LA and LL). It does not comprise an inductor. Split resistors are used that allow the use of resistor elements with reduced voltage rating for small physical size. Further, split electrical contacts of the ECG electrode are used that support simple detection if the ECG electrode is connected or not.

Figure 12:
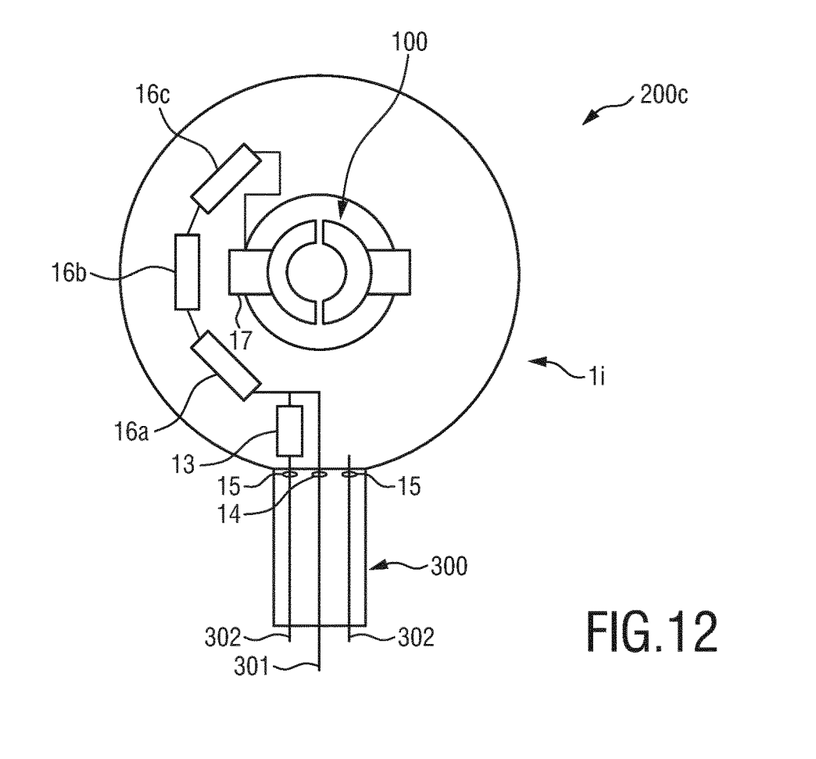
FIG. 12 shows a top view of an ECG cable including an embodiment of an ECG electrode connector that is not intended for respiration measurement.

FIG. 12 shows a top view of an ECG cable 200c including an embodiment of an ECG electrode connector 1i that is intended for all other leads (e.g. RL and V1-V6). It does not comprise an inductor. The lead wire 300 in this embodiment comprises a single signal line 301. The ECG electrode connector 1i comprises a single safety network.

Figure 13:
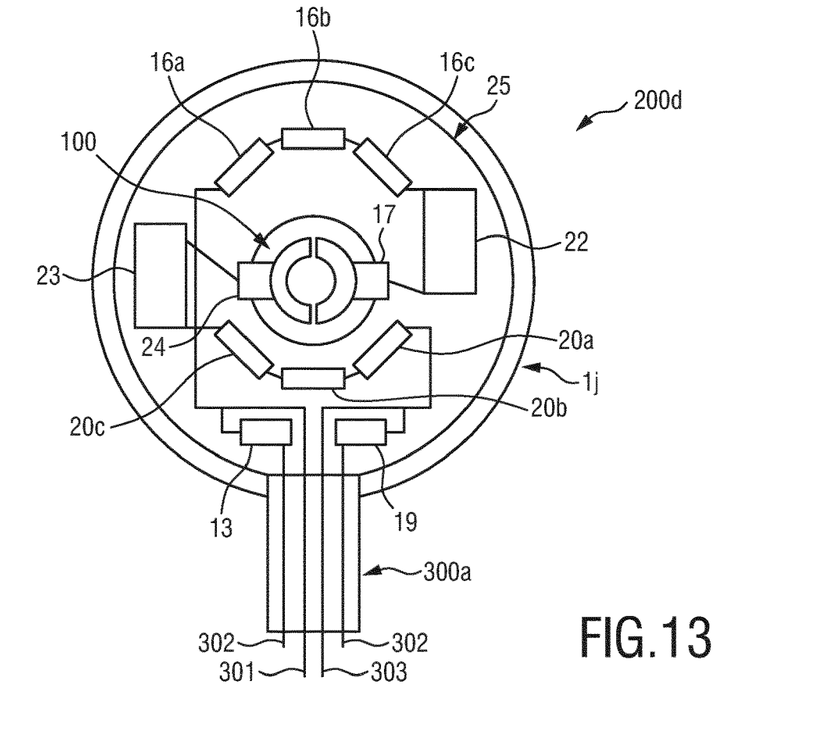
FIG. 13 a top view of an ECG cable including an embodiment of an ECG electrode connector with shield.

One or multiple small PCBs may be embedded inside the ECG electrode connector to hold the safety elements. Such a PCB may have multiple conducting layers. One layer can be used as shield. This would reduce the sensitivity of the ECG measurement system to interference. FIG. 13 shows a top view of an ECG cable 200c including an embodiment of an ECG electrode connector 1j with shield. A ground plane 25 covers the largest part of the ECG electrode 100, in particular near the safety elements, and is electrically connected to the shield 302 of the lead wire 300a.

Figure 14:
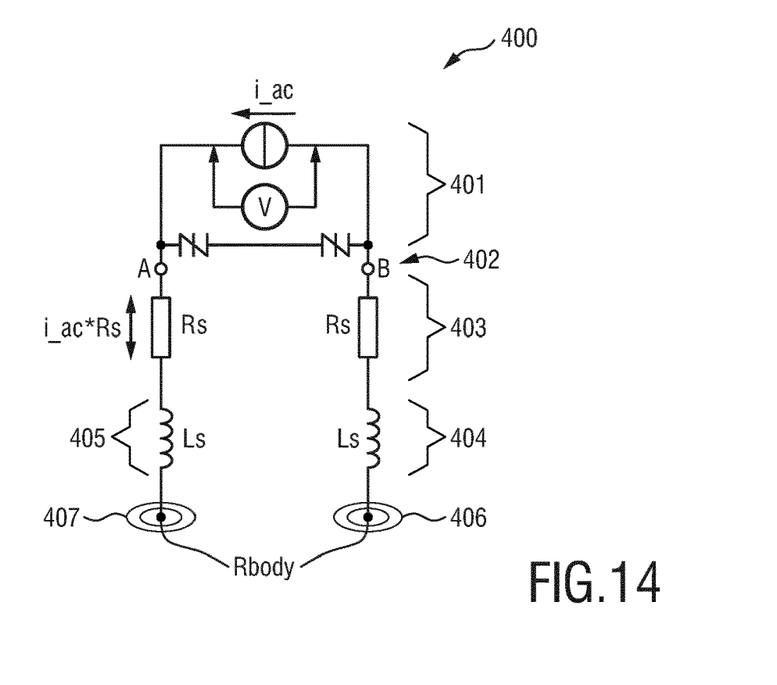
FIG. 14 shows a circuit diagram of an embodiment of a known respiration measurement system.

In a conventional ECG measurement system, the partitioning of elements from the ECG measurement unit to the ECG electrodes is shown FIG. 14 depicting an embodiment of a known respiration measurement system 400. It comprises an impedance measurement unit 401, a connector 402, a trunk cable 403, ECG electrode connectors 404, 405 and ECG electrodes 406, 407. The respiration impedance measurement system (inside the impedance measurement unit) drives an AC-current i_ac to the patient's body and measures the resulting voltage V across nodes A, B. The actual measured impedance is the series impedance of Rbody+2·Z_electrode+2·Z_Ls+2 Rs. The voltage clamping elements are conventionally placed inside the impedance measurement unit 401. ESU protection inductors Ls are embedded in the ECG electrode connectors 404, 405. The trunk cable 403 includes the safety series resistors Rs.

In a 2-wire respiration measurement system, the resistors Rs have a typical value of Rs=1 kΩ. The value of Rs is limited because a higher Rs results in reduced accuracy of the measurement of Rbody. Lower-ohmic resistors Rs are preferred for accurate Rbody measurement, but dissipate more energy when a patient is undergoing defibrillation treatments and thus need to be large in physical size.

Figure 15:
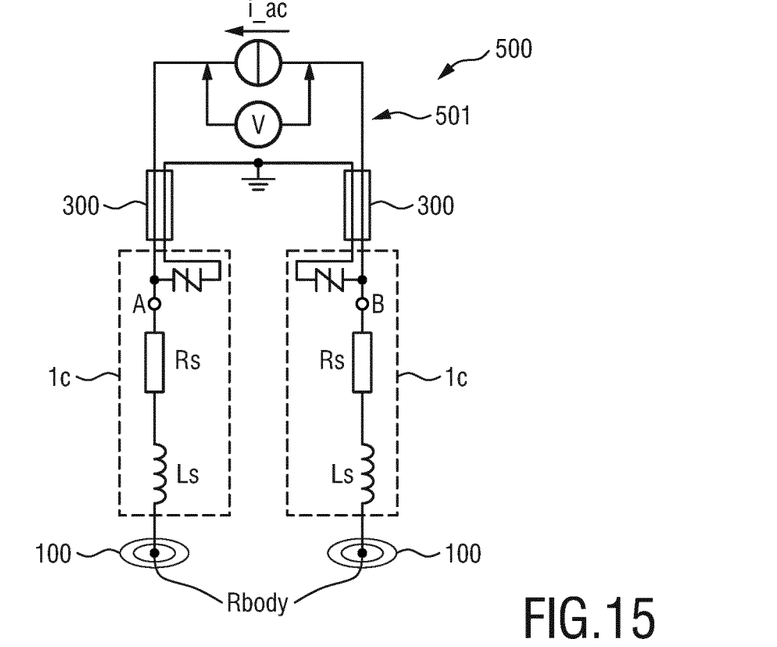
FIG. 15 shows a circuit diagram of an embodiment of a respiration measurement system according to the present invention.

FIG. 15 shows a circuit diagram of a first embodiment of a respiration measurement system 500 according to the present invention. It comprises an impedance measurement unit 501 and, per ECG electrode 100, a lead wire 300 and an ECG electrode connector 1a. Compared to the conventional respiration measurement system 400 shown in FIG. 14, the trunk cable is completely omitted and the safety elements are all placed in the ECG electrode connectors 1c as shown in FIG. 5.

Figure 16:
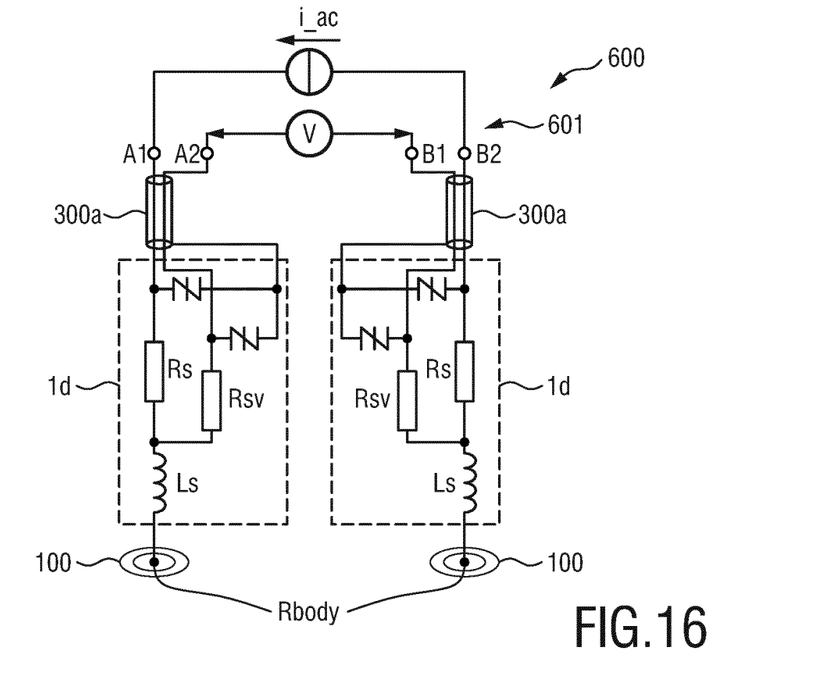
FIG. 16 shows a circuit diagram of an embodiment of an ECG measurement system according to the present invention.

The measurement of Rbody can be done more accurate using a 4-wire impedance measurement system. FIG. 16 shows a circuit diagram of a second embodiment of an ECG measurement system 600 according to the present invention using such a 4-wire impedance measurement system 601. The ECG measurement system 600 comprises, besides the 4-wire impedance measurement unit 601, per ECG electrode 100, a lead wire 300a (comprising two signal wires and a shield, as e.g. shown in FIG. 10) and an ECG electrode connector 1d as shown in FIG. 6.

In the 4-wire respiration measurement, the measured impedance equals Rbody+2·Z_electrode+2·Z_Ls. The value of Rsv does not play a role in the measured impedance because the voltage is measured behind the series resistance Rs in the modulator path, at the side of the inductor. The series resistances Rsv in the voltage measurement path are required for protection but are not seen in the measured impedance because there is no current i_ac in Rsv. As a result, the 4-wire respiration measurement method provides an improved and more reliable approach for Rbody measurements. The impedance from the inductors Ls is still seen in series with Rbody.

Since, in the 4-wire impedance measurement method, resistors Rs and Rsv are both not seen in the impedance measurement, their values can be increased with respect to the original 2-wire configuration shown in FIG. 15. For example, Rs=Rsv=10 kΩ can be used. The increased resistance results in a reduced energy dissipation during defibrillation treatments. Therefore, resistors of smaller physical size can be used for the 4-wire respiration measurement system compared to the 2-wire configuration shown in FIG. 15.

Contrary to a conventional ECG measurement system, in which there is still a trunk unit present in which the voltage clamping elements are placed, according to the ECG measurement system depicted in FIG. 16 the trunk unit is eliminated. Safety and protection components (resistor, voltage clamping element and inductor) are placed inside each ECG electrode connector 1d. Each ECG electrode connector 1d is connected to the impedance measurement system 601 via a lead wire 300. The ECG electrodes 100 that can take part in the respiration measurement system have duplicate safety networks (voltage clamping element and resistor).

From an electrical perspective, the measurement system 600 according to the present invention and a comparable conventional measurement system using a trunk cable are substantially equal and their performance is identical. The proposed partitioning with safety elements inside the ECG electrode connectors is possible and advantageous in combination with 4-wire respiration detection, since the 4-wire method allows for increased resistance values Rs and Rsv, as explained above, which dissipate less energy from a defibrillation pulse and thus can be smaller in size.

Figure 17:
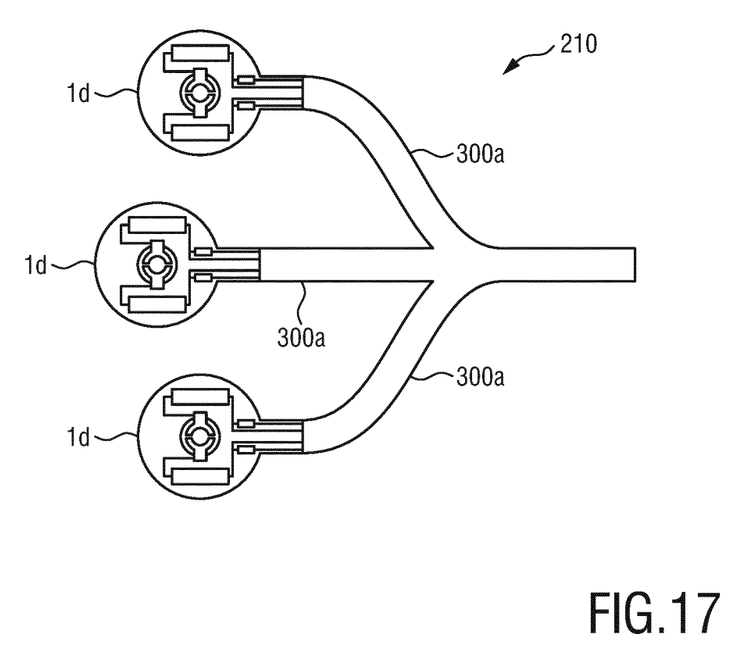
FIG. 17 shows a diagram of another embodiment an ECG cable using identical ECG electrode connectors.

FIG. 17 shows a diagram of an exemplary realization of an ECG cable 210 (also called ECG lead set) interfacing to three ECG electrodes by use of three lead wires 300a. The protection network is embedded in the ECG electrode connectors 1d, supporting 4-wire respiration measurement.

Figure 18:
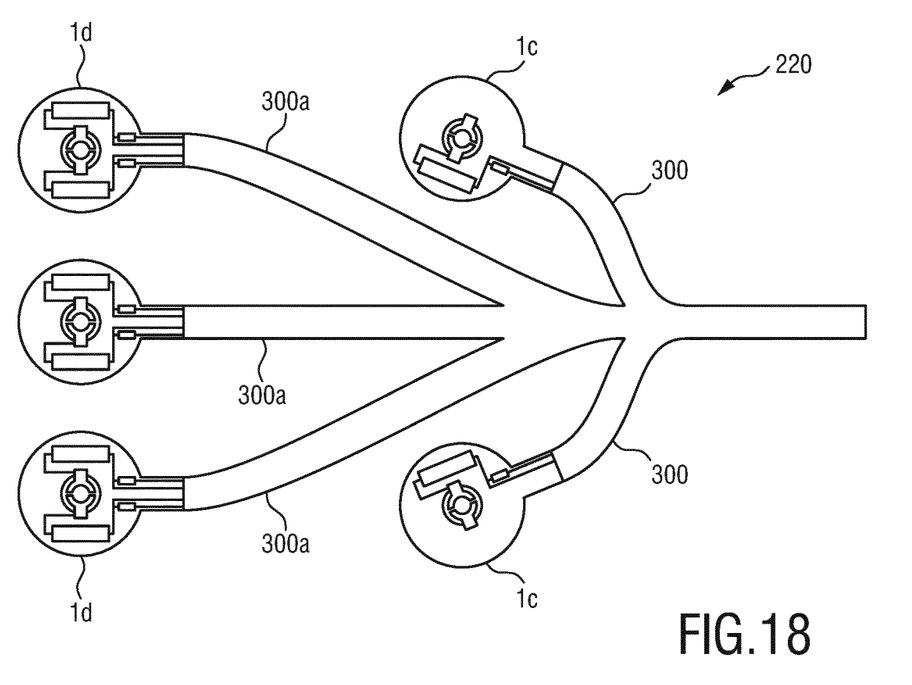
FIG. 18 shows a diagram of another embodiment an ECG cable using different ECG electrode connectors.

FIG. 18 shows a diagram of another exemplary realization of an ECG cable 220 using different ECG electrode connectors supporting five ECG electrodes via five lead wires. Three ECG electrode connectors 1d and the corresponding respiration-type lead wires 300a are configured for 4-wire respiration measurement and two ECG electrode connectors 1c and the corresponding non-respiration type lead wires 300 are not configured for 4-wire respiration measurement.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An ECG electrode connector for mechanically and electrically connecting an external ECG electrode with a lead wire, the ECG electrode connector comprising:
   a connection arrangement for mechanically connecting the ECG electrode connector with the external ECG electrode;
   a lead wire terminal for connection with a signal line of a lead wire;
   a shield terminal for connection with a shield of the lead wire;
   an electrode contact for contacting an electrical contact of the ECG electrode;
   a voltage clamping element electrically coupled between the lead wire terminal and the shield terminal;
   a resistor electrically coupled between the lead wire terminal and the electrode contact; and
   an inductor coupled between the lead wire terminal and the electrode contact.

2. The ECG electrode connector as claimed in claim 1, wherein the resistor comprises two or more resistor elements coupled in series.

3. The ECG electrode connector as claimed in claim 1, further comprising a ground plane coupled to the shield terminal and arranged between the resistor and the voltage clamping element on a first side and the ECG electrode on a second side, when the ECG electrode connector and the ECG electrode are connected.

4. The ECG electrode connector as claimed in claim 1, wherein the connection arrangement comprises a clamping arrangement or a snapping arrangement or a grabbing arrangement.

5. The ECG electrode connector as claimed in claim 1, further comprising:
   a second lead wire terminal for connection with a second signal line of the lead wire,
   a second voltage clamping element coupled between the second lead wire terminal and the shield terminal, and
   a second resistor coupled between the second lead wire terminal and the electrode contact.

6. The ECG electrode connector as claimed in claim 5, wherein one end of the inductor is coupled to the electrode contact and the other end of the inductor is coupled to the resistor and the second resistor.

7. The ECG electrode connector as claimed in claim 5, further comprising a second inductor coupled between the second lead wire terminal and the electrode contact.

8. The ECG electrode connector as claimed in claim 7, further comprising a second electrode contact for contacting a second electrical contact of the ECG electrode, wherein the inductor is coupled to the electrode contact and the second inductor is coupled to the second electrode contact.

9. The ECG electrode connector as claimed in claim 1, wherein the resistor has a resistance of at least 2kΩ.

* * * * *